United States Patent [19]
White

[11] Patent Number: 5,405,005
[45] Date of Patent: * Apr. 11, 1995

[54] PACKAGE FOR HIP PROSTHESIS
[75] Inventor: Mark White, Memphis, Tenn.
[73] Assignee: Smith & Nephew Richards Inc., Memphis, Tenn.
[*] Notice: The portion of the term of this patent subsequent to Mar. 16, 2010 has been disclaimed.
[21] Appl. No.: 33,614
[22] Filed: Mar. 16, 1993

Related U.S. Application Data

[63] Continuation of Ser. No. 728,000, Jul. 10, 1991, Pat. No. 5,193,679.
[51] Int. Cl.⁶ .............................................. A61B 19/00
[52] U.S. Cl. ................................... 206/363; 206/438; 206/467; 220/4.23; 220/4.24
[58] Field of Search ............... 206/438, 363, 467, 470, 206/471, 461, 564; 220/4.22, 4.23, 4.24; 264/DIG. 30; 425/2, 451.9

[56] References Cited

U.S. PATENT DOCUMENTS

| 3,556,158 | 1/1971 | Schneider | 220/4.24 X |
| 4,126,239 | 11/1978 | Gehrig et al. | 220/4.23 X |
| 4,512,471 | 4/1985 | Kaster et al. | 220/4.24 X |
| 4,512,474 | 4/1985 | Harding | 220/4.23 X |
| 4,750,619 | 6/1988 | Cohen et al. | 206/438 |
| 4,971,737 | 11/1990 | Infanti | 264/DIG. 30 X |
| 5,193,679 | 3/1993 | White | 206/363 |

Primary Examiner—Jacob K. Ackun
Attorney, Agent, or Firm—Pravel, Hewitt, Kimball & Krieger

[57] ABSTRACT

A clamshell package supports a hip prosthesis so that modular pads and/or a modular distal sleeves can be added during surgery so that sterility is maintained while achieving a custom fit for the patient.

6 Claims, 5 Drawing Sheets

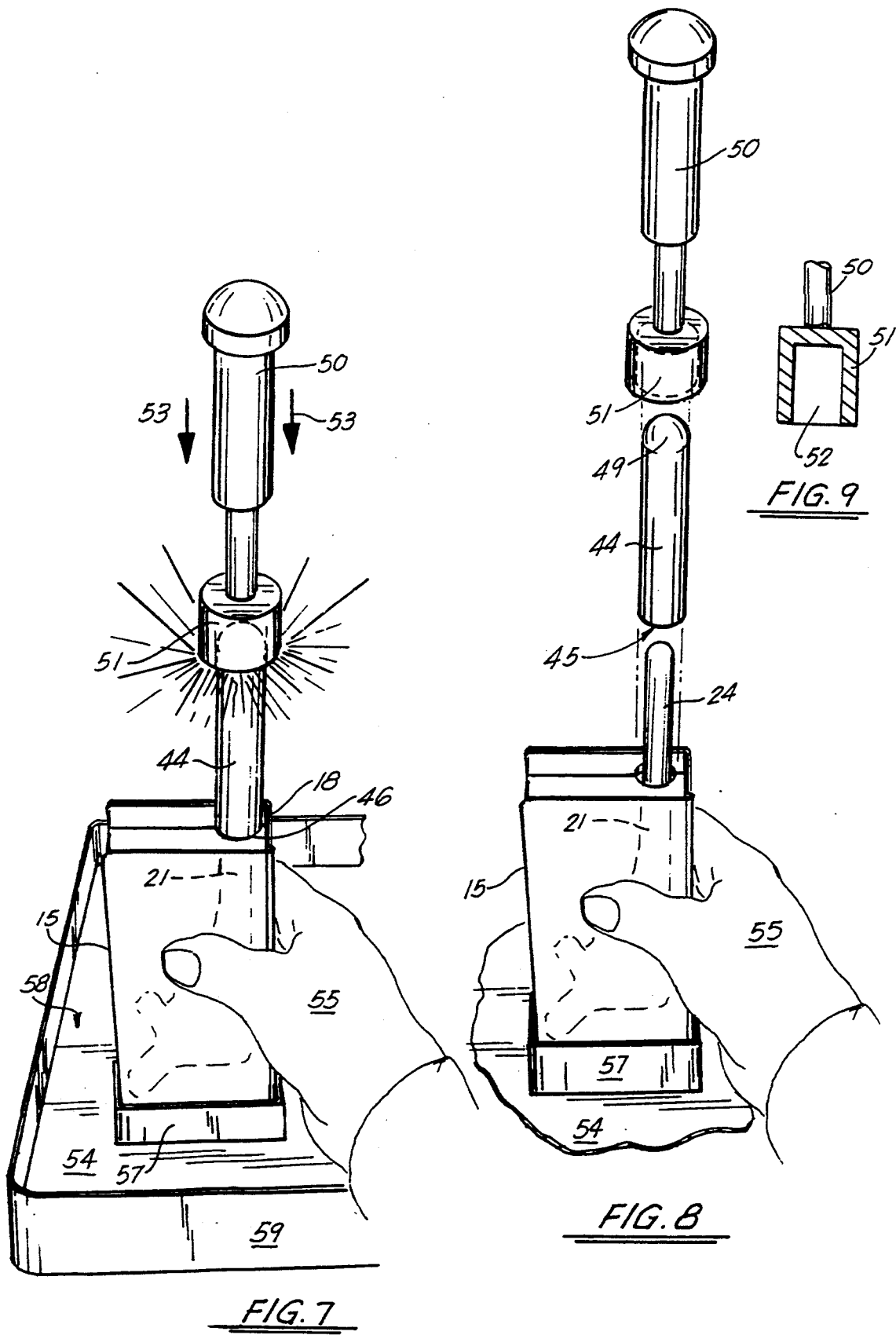

PACKAGE FOR HIP PROSTHESIS

This is a continuation of application Ser. No. 07/728,000, filed on Jul. 10, 1991, now U.S. Pat. No. 5,193,679.

BACKGROUND OF THE INVENTION

1. Field of the Invention

The present invention relates to packages for prosthetic devices, and more particularly a package for supporting a hip stem/hip prosthesis wherein a cassette having half portions supports the prosthesis at least around the proximal end thereof so that modular pads and modular distal sleeves can be assembled thereto while supported by the packages, prior to hip stem surgery.

2. General Background

There are a number of hip prosthetic devices that are commercially available which use a configuration that includes a lower stem which is generally cylindrical, a larger proximal end portion that includes anterior and posterior surfaces, and also a neck region to which can acetabular ball is affixed.

There are commercially available modular hip implant systems that provide proximal modules and distal modules. Because of the irregular shape of such hip implants and of the protruding modular parts which are to be added (such as modular pads and distal sleeves), complete assembly on a surgical table and during surgery can be very difficult. Another problem is that sterility must be maintained during installation of modular parts and removal of the implant from its package during surgery.

There are four commercially modular hip systems known to the Applicant, each of which addresses this problem in a different manner.

The Infinity hip system from Dow Corning Wright uses a vise to clamp the stem in place while the proximal module is applied with a mallet. This vise is cumbersome and could possibly cause damage to the stem. This implant system does not use a distal sleeve.

The Omni-Flex hip from Osteonics has a distal sleeve which is applied by laying the stem end up on the proximal end and pounding the distal sleeve in place with a mallet. This method can potentially cause problems because it allows the trunnion to rest on the table where it can possibly be damaged. Also the hip stem could possibly be knocked off the table during this installation, damaging the hip and compromising sterility.

The S-ROM Hip, from Joint Medical Products, has a proximal module which is placed in the femur first followed by the stem which is tapped into place at the proper orientation. This stem is assembled in the femur as opposed to preassembly.

The APR II, from Intermedics, has an open ended distal sleeve which is applied by using an impactor which is struck with a mallet.

An example of a modular hip prosthesis system can be seen in U.S. Pat. No. 4,995,883, entitled "Modular Hip Prosthesis", issued Feb. 26, 1991, and assigned to the assignee of this application, Smith & Nephew Richards Inc.

There are some patented constructions for packages and package assemblies that have been patented. As an example, U.S. Pat. No. 4,921,096, issued to Taut, Inc. describes a package assembly for a pointed surgical instrument. One part of the package comprises a clamshell-type portion which is openable so that the non-pointed end of the instrument can be grasped and the instrument removed or replaced in the package without touching the pointed end. The clamshell portion may be open or closed as required. The package is in two parts which are hinged together. One part cannot be opened and encloses the sharp point. The other part has the clamshell-type opening whereby when opened the non-sharp end of the product may be grasped to remove it from the package. After use, the product may be reintroduced into the package, the clamshell opening is closed again and the package may be disposed of.

U.S. Pat. No. 4,872,551 describes a clamshell blister pack for pliers wherein the head of the pliers is held in the pack and the handles can be manipulated by the customer. The package in the '551 patent includes a pair of opposing mirror-image panels having recesses and joined along a common lower end to form a base portion. The base portion is provided with a pair of openings for accommodating the handles of the pliers. The head of the pliers is held in the package but the handles protrude from the base of the package and can be manipulated to a specified extent by the customer prior to purchase without opening the package.

SUMMARY OF THE INVENTION

Each of the above discussed systems addresses the assembly problem in a slightly different way. However, the design of the present invention is unique because it provides protection for the product during shipping and maintains sterility until the product is ready for use. In the operating room, the package then becomes an assembly device which can be disposed of after the surgery. Because the clamshell supports the prosthesis, the implant cannot slide or tilt during assembly, which could cause the sleeve or pad to have inadequate engagement with the stem. By using the package of the present invention, the surgeon can be insured that the sleeves and pads will be applied consistently every time. Some modular systems which do not have a fixture, run the risk of improper seating of the modules due to movement or rocking of the prosthesis.

The present invention thus provides an improved instrument package intended for use with a medical prosthesis such as modular hip prosthesis system of the type, e.g., shown and described in U.S. Pat. No. 4,995,883, entitled "Modular Hip Prosthesis", issued Feb. 26, 1991, and incorporated herein by reference.

The present invention provides a package with a cassette having two trays and a hinged web component which snaps around the implant to encase it.

During surgery, the proper pre-selected modular pads and or distal sleeves are opened along with the package. The prosthesis and cassette assembly is then placed end up on the operating room table, and the distal sleeve can be driven onto the stem using a spring loaded driver. The cassette is then opened and the pads are driven into place using an impact driver instrument. Two snaps are used to keep the cassette from opening during impact.

The present invention provides a container for the carriage of a modular hip prosthesis having a lower stem, a proximal portion with anterior and posterior sides, a neck portion, and modular pads and/or a distal sleeve. The apparatus includes a cassette having a pair of halves of corresponding size, each having a face that abuts the face of the other upon closure, and each half having a recess that conforms generally to the outer surface of the prosthesis.

A bore of the cassette is formed upon closure, the bore surrounding at least a lower end portion of the stem of the prosthesis and extending between the recesses so that a distal sleeve can be added to the stem while the prosthesis is occupying a position in the cassette.

The cassette has a shape that closely supports the entire proximal end of the prosthesis so that modular pad can be added to the prosthesis while the prosthesis is being supported by the cassette.

Each cassette half preferably has a recess that cradles an anterior or posterior half of the prosthesis.

The cassette is comprised of a web member that connects the cassette halves at respective peripheral portions of each cassette half.

A bore is provided that defines a cylindrical opening upon closure of the cassette halves that encircles the stem.

The bore is generally cylindrical and preferably of uniformed diameter.

The cassette is generally rectangularly shaped having parallel side wall portions and the prosthesis is oriented along an axial line that is generally parallel to the parallel side walls of the cassette.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein:

FIG. 7 is a perspective view of the preferred embodiment of the apparatus of the present invention illustrating the use of an impact driver to add a distal sleeve to the prosthesis;

FIG. 8 is another perspective view of the preferred embodiment of the apparatus of the present invention illustrating an impact driver, distal sleeve, and prosthesis in exploded perspective view; and FIG. 9 is a fragmentary sectional view of the impact driver of FIG. 8.

DETAILED DESCRIPTION OF THE PREFERRED EMBODIMENT

Figure 1:
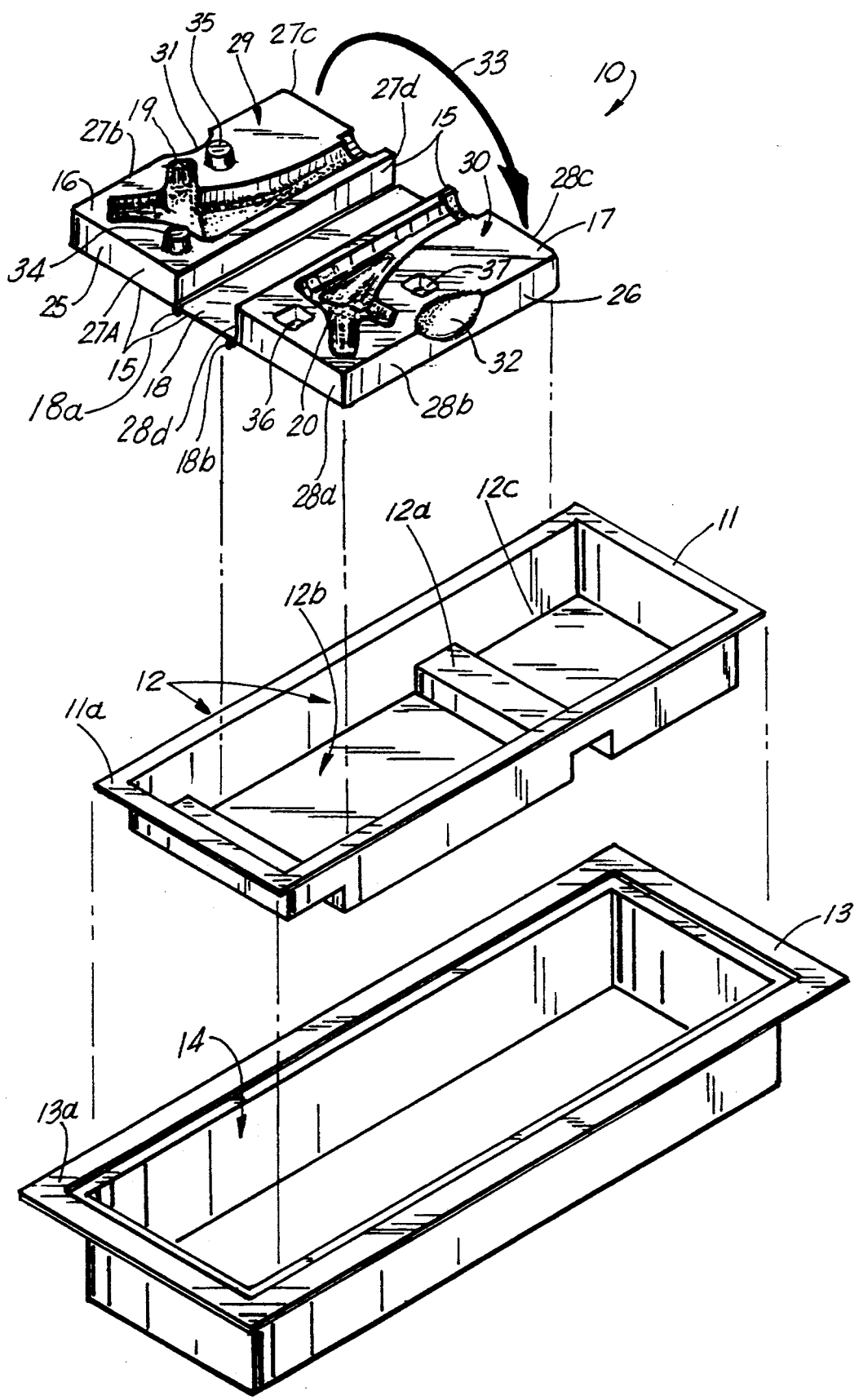
FIG. 1 is a perspective exploded view of the preferred embodiment of the apparatus of the present invention.
Figure 2:
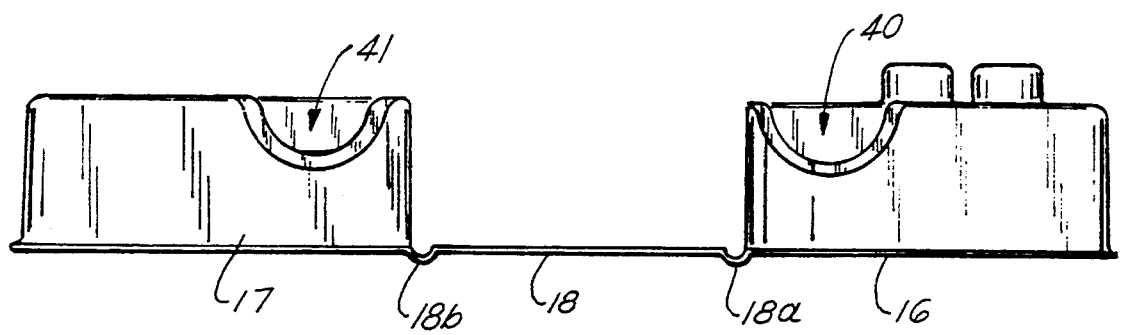
FIG. 2 is an end view of the preferred embodiment of the apparatus of the present invention shown in a fully opened positioned.

FIGS. 1–6 illustrate the preferred embodiment of the apparatus of the present invention designated generally by the numeral 10. Prosthesis package apparatus 10 includes a first plastic tray 11 having a well 12 which is separated into well sections 12b, 12c with divider 12a.

A second plastic tray 13 includes a well 14 for receiving the plastic tray 11 thereinto. The well section 12b receives clamshell cassette 15. In the preferred embodiment, a hip prosthesis 21 (see FIG. 6) extends out the end of the cassette 15 so that a distal sleeve can be added thereto using an impact driver. Each tray 11, 13 can have a peripheral flange 11a, 13a respectively to which release liners (not shown) can be affixed with adhesive, for example, so that the contents of each tray 11, 13 can be maintained sterile.

The clamshell cassette 15 includes a pair of cassette half portions 16, 17 connected together with longitudinally extending web 18. Each cassette half 16, 17 provides respective storage depressions 19, 20 each conforming to the outer surface of a hip prosthesis body 21. The prosthesis body 21 and each storage depression 19, 20 include neck region 22, proximal section 23, and a distal stem section 24. Each cassette half 16, 17 includes a peripheral side wall 25, 26 respectively, the peripheral side wall 25 being comprised of wall sections 27a–d and the peripheral side wall 26 being comprised of wall sections 28a–d.

Figure 3:
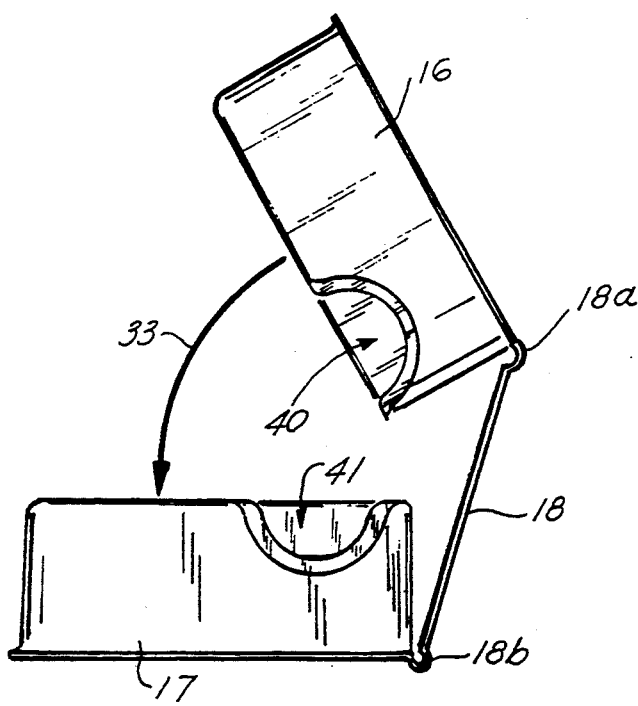
FIG. 3 is an end view of the preferred embodiment of the apparatus of the present invention illustrating closure.

Each cassette half 16, 17 respectively provides an interior face 29, 30 portion, the faces 29, 30 abutting upon closure of the cassette 15. Each cassette half is equipped with a curved recess for placement of the users thumb, including thumb recesses 31, 32 that assist in opening halves 16, 17. Arrow 33 in FIGS. 1 and 3 illustrates closure of the cassette halves about hinges 18a, 18b. The cassette halves 16, 17 can be maintained in a closed position as shown in FIGS. 5 and 6 by the attachment of a pair of closure snaps 34, 35 into correspondingly placed snap wells 36, 37.

Figure 4:
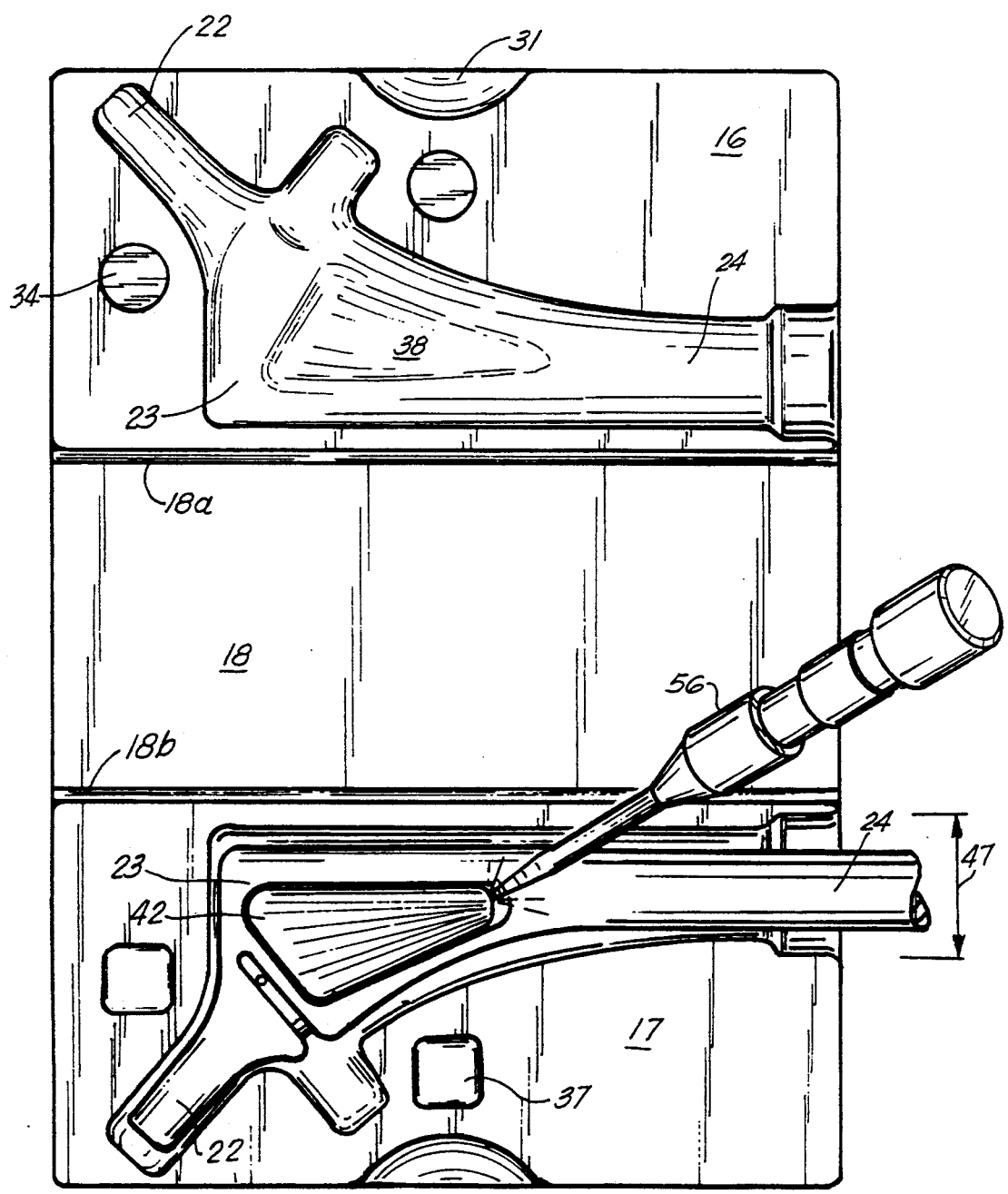
FIG. 4 is a top view of the preferred embodiment of the apparatus of the present invention in a fully opened position.
Figure 5:
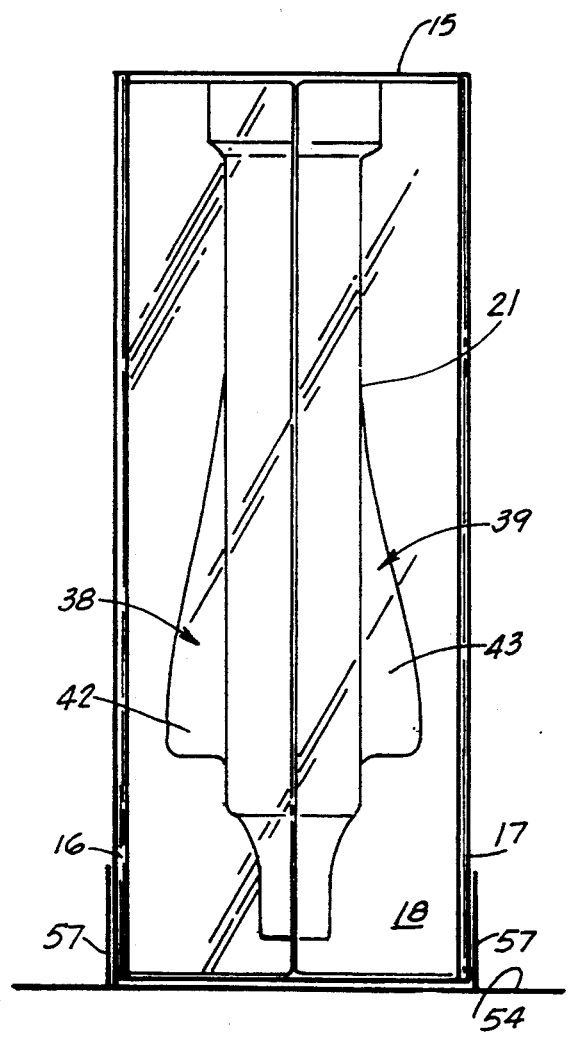
FIG. 5 is a side view of the preferred embodiment of the apparatus of the present invention.
Figure 6:
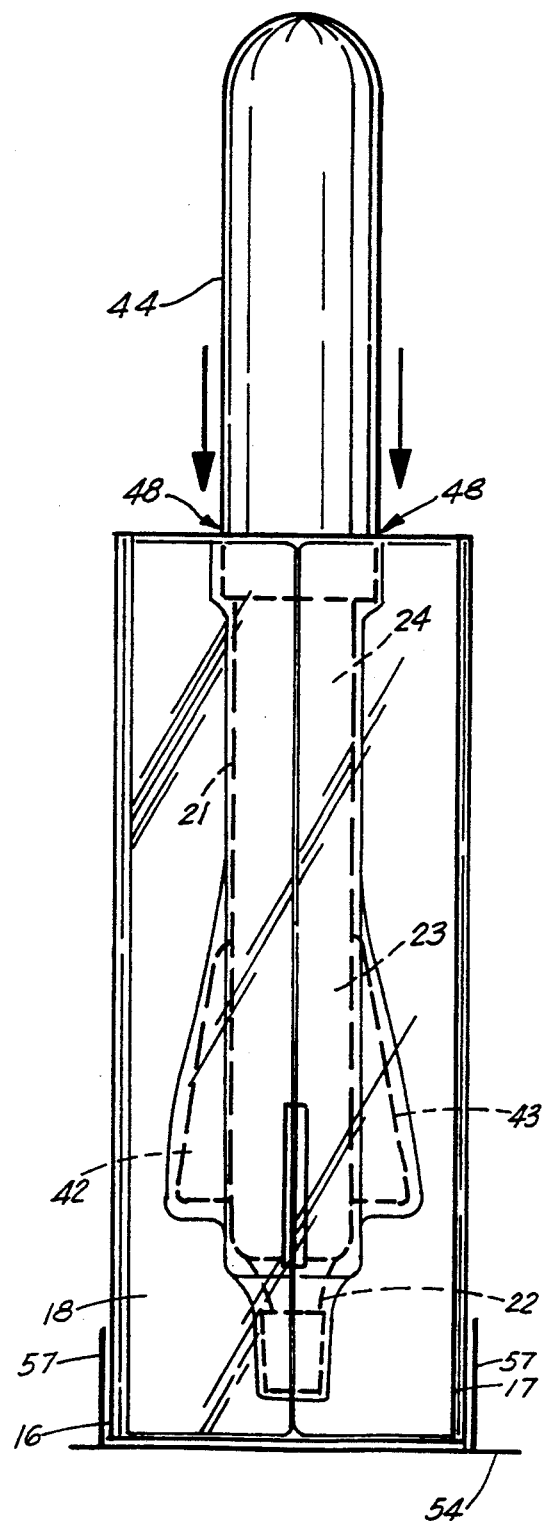
FIG. 6 is a side view of the preferred embodiment of the apparatus of the present invention illustrating the addition of a distal sleeve to the prosthesis.

Each storage depression 19, 20 is preferably of corresponding size, with the storage depressions 19, 20 respectively containing an anterior or a posterior half portion of the prosthesis 21 upon closure, as illustrated in FIGS. 5 and 6. Each depression 20, 21 includes a depression for a modular pad, the pad depressions being designated as 38, 39 respectively. Each cassette half 16, 17 includes semicircular opening 40, 41. The semicircular openings 40, 41 define a distal sleeve opening 46 upon closure, as shown in FIG. 8. In FIG. 4, installation of a modular pad 42 is shown using impact driver 56. The driver 56 loads the pad into it recess and the casette half 17 supports the prosthesis 21.

Distal sleeve 44 has a sleeve bore 45 with an internal diameter that is sized to fit upon the distal stem 21 portion of the prosthesis 21. Internal diameter 47 of sleeve opening 46 is larger than the external diameter of sleeve 44, as shown in FIGS. 4, 5, and 6. In this fashion, the entire prosthesis 21 can be closely conformed to the depressions 19, 20 while the opening 46 is sized to receive the larger diameter distal sleeve 44.

FIGS. 7 and 8 illustrate attachment of a distal sleeve 44 to the stem 24 portion of the prosthesis 21. The cassette 15 is first supported in a closed position with the stem 24 extending outwardly of the opening 46. The distal sleeve 44 is then placed upon the distal stem by registering the distal stem 24 into the internal bore 45 of the distal sleeve 44. An impact driver 50 having a tool tip portion 51 is placed upon the hemispherical end 49 of the distal sleeve 44.

A hemispherical recess 52 can be provided on the tool tip 51. The impact driver 50 then applies a load to the distal sleeve forcing it on the distal stem. During this operation, the closed cassette 15 fully supports the prosthesis 21 during the impact driving. Arrows 53 illustrate the direction of movement of the distal sleeve 44 onto the distal stem 24. An instrument tray 54 having an interior 58 can have rectngular receptacle 57 sized to receive the cassette 15. The receptacle can be used to support the cassette 15 during installation of the modular sleeve 44. When installing the sleeve 44, receptacle 57 in instrument tray 54 surrounds the lower end of and supports the cassette 15. Because the apparatus 10 can be sterile, protecting the sterility of prosthesis 21, the user's hand 55 can be any operating room person, such as a doctor or nurse, wearing sterile gown and gloves. Thus, the present invention maintains a sterile integrity of the prosthesis 21 yet allowing change in prosthesis size and shape using the modular components.

It should be understood from the above that the entire cassette 15, prosthesis 21, modular pads 42, 43 and distal sleeve 44 can be maintained in a sterile condition during the entire surgery. The prosthesis can be custom sized for a particular patient with minimum risk of damage to the prosthesis or of contamination of the prosthesis.

The following table lists the part numbers and part descriptions as used herein and as appearing in the attached drawings.

TABLE

PARTS LIST

| Part Number | Description |
| --- | --- |
| 10 | package |
| 11 | plastic tray |
| 11a | peripheral flange |
| 12 | well |
| 12a | divider |
| 12b–12c | well sections |
| 13 | plastic tray |
| 13a | peripheral flange |
| 14 | well |
| 15 | clamshell cassette |
| 16 | cassette half |
| 17 | cassette half |
| 18 | web |
| 18a–18b | hinges |
| 19 | storage depression |
| 20 | storage depression |
| 21 | hip prosthesis |
| 22 | neck region |
| 23 | proximal section |
| 24 | distal stem |
| 25 | peripheral sidewall |
| 26 | peripheral sidewall |
| 27a–d | wall sections |
| 28a–d | wall sections |
| 29 | inside face |
| 30 | inside face |
| 31 | thumb recess |
| 32 | thumb recess |
| 33 | arrow |
| 34 | closure snap |
| 35 | closure snap |
| 36 | snap well |
| 37 | snap well |
| 38 | depression for pad |
| 39 | depression for pad |
| 40 | semicircular opening |
| 41 | semicircular opening |
| 42 | modular pad |
| 43 | modular pad |
| 44 | distal sleeve |

TABLE-continued

PARTS LIST

| Part Number | Description |
| --- | --- |
| 45 | sleeve bore |
| 46 | sleeve opening |
| 47 | internal diameter |
| 48 | impact tool opening |
| 49 | distal end |
| 50 | impact tool |
| 51 | tool tip |
| 52 | tool tip recess |
| 53 | arrows |
| 54 | instrument tray |
| 55 | users hand |
| 56 | impact driver |
| 57 | instrument tray receptacle |
| 58 | instrument tray interior |
| 59 | instrument tray sidewall |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as the invention is:

1. A system for containing a sterile orthopedic prosthesis comprising:
    a) an orthopedic prosthesis with a prosthesis body and having one or more modular parts to be connected to the body;
    b) a cassette that can be opened and closed, comprising a pair of cassette halves of corresponding size, each having a face that abuts the face of the other upon closure, and each half having a recess that conforms to the outer surface of the orthopedic prosthesis;
    c) the recesses defining a bore of the cassette when the cassette is closed, the bore closely conforming to the entire outer surface of the prosthesis; and
    d) an outer housing having an interior that can contain the cassette, enabling the cassette and prosthesis in combination to be sterilized after placement in the housing for providing a sterile environment to the medical prosthesis.

2. The apparatus of claim 1 wherein the prosthesis has anterior and posterior portions and each cassette half has a recess that cradles at least an anterior or a posterior portion of the prosthesis.

3. The apparatus of claim 1 wherein the cassette is further comprised of a web member that connects the cassette halves at respective peripheral portions of each cassette half so that the web holds the halves together when the cassette is opened.

4. The apparatus of claim 1 further comprising a release liner that registers upon the outer housing for sealing the interior.

5. The apparatus of claim 1 wherein the outer housing has a peripheral flange portion that defines an attachment for the release liner to the outer housing.

6. The apparatus of claim 1 wherein the cassette is generally rectangularly shaped and having parallel side wall portions, and the prosthesis is oriented along an axial line that is generally parallel to the parallel side walls.

* * * * *